United States Patent [19]
Eibofner

[11] 3,934,349
[45] Jan. 27, 1976

[54] DENTAL HANDPIECE OR ELBOWS FOR MOUNTING DENTAL TREATMENT TOOLS

[75] Inventor: Eugen Eibofner, Mettenberg, Germany

[73] Assignee: Kaltenbach & Voigt, Biberach an der Riss, Germany

[22] Filed: Nov. 5, 1973

[21] Appl. No.: 412,722

[30] Foreign Application Priority Data
Nov. 15, 1972 Germany............................ 2256059

[52] U.S. Cl. .................................................. 32/27
[51] Int. Cl.² ........................................... A61C 1/10
[58] Field of Search ......... 279/9, 1 R, 1 ME; 32/27, 32/26

[56] References Cited
UNITED STATES PATENTS
1,920,934  8/1933  Keen................................ 76/DIG. 4
3,787,977  1/1974  Farian et al............................ 32/27

*Primary Examiner*—Robert Peshock
*Attorney, Agent, or Firm*—Haseltine, Lake & Waters

[57]  ABSTRACT

A dental handpiece or elbow having a guide sleeve for mounting a dental treatment tool, in which the inner annular surface of the guide sleeve is coated with a wear-resistant coating so as to enhance the strength thereof against hammering and radial forces generated during use of the handpiece. In the case where the sleeve is connected to the tool through the intermediary of a collet, the latter is also provided with a similar coating in at least the regions in contact with the guide sleeve.

4 Claims, 3 Drawing Figures

DENTAL HANDPIECE OR ELBOWS FOR MOUNTING DENTAL TREATMENT TOOLS

FIELD OF THE INVENTION

The present invention relates to dental handpieces or elbows.

DISCUSSION OF THE PRIOR ART

In presently known dental handpieces or elbows which have guide sleeves of hardened metal adapted to receive the shank of a dental treatment tool, the above-mentioned guide sleeve is subjected to hammering forces, caused on the one hand by the required operative tolerance or fit at the forward end of the guide sleeve, and at the other end thereof through the chattering contact by the cutters of the dental drill or grinding tools. These forces occur irrespective as to whether the guide sleeve is formed for directly receiving the tool, or whether an intermediate collet is positioned between the particular guide sleeve and the tool shank. Due to the radial loads experienced at the tool tip during operation, there is generated an additional force which, in particular at both ends of the guide sleeve, is also transmitted in the radial direction.

In view of these forces the guide sleeve is subjected at both of its ends to a mostly trumpet-shaped enlargement, independently of whether the guide sleeve is or is not formed of a hardened metal. The result thereof is the rough operation of the dental treatment tool, leading to the rapid destruction of the latter. Furthermore, operation on or treatment of a natural tooth with the required degree of precision becomes thereby impossible.

It has further been attempted to construct the particular sleeves for receiving the shank of a dental treatment tool of suitable hard metal or alloy. This, however, is not possible if the sleeves are constructed of a plurality of pieces, and with particularly highly-stressed sleeve portions being formed of hard metal or sapphire. One such construction has become known, for example, from German Pat. No. 1,018,583. These multi-sectioned constructions, however, cause difficulties in the manufacture of and upon assembly of the guide sleeve, in effect the positioning of the sections, which in particular is dependent upon the extremely small dimensions of the individual elements or sections. Consequently, achieving precise alignment of the individual pieces of the guide sleeve becomes extremely difficult.

SUMMARY OF THE INVENTION

Accordingly, it is an object of the present invention to provide a dental handpiece or elbow in which the guide sleeve has a coating applied thereto enhancing its resistance against hammering and radial forces, so as to allow for a simple construction thereof.

Through lengthy investigations it has been determined that, in contrast with known constructions, it is possible to attain a reduction in abrasion caused by hammering, respectively, radial or other generated forces to a value of one-sixth of normal wear.

A particularly advantageous degree of resistance to abrasion of the guide sleeve, as compared to the prior art, is obtained when the layer or coating material is constituted, for example, of chromium and metal carbides.

Additional life expectancy and superior characteristics are also imparted to the guide sleeve when the surface coating is very smooth. The roughness of the surface may be reduced by a considerable extent upon the inner wall of the sleeve, after deposition thereon of the hardened coating, is polished by means of a suitable diamond-polishing tool.

BRIEF DESCRIPTION OF THE DRAWINGS

Preferred embodiments of the dental handpiece or elbow of the invention are now described in the following detailed description thereof, taken in conjunction with the accompanying drawings, in which.

DETAILED DESCRIPTION

Figure 1:
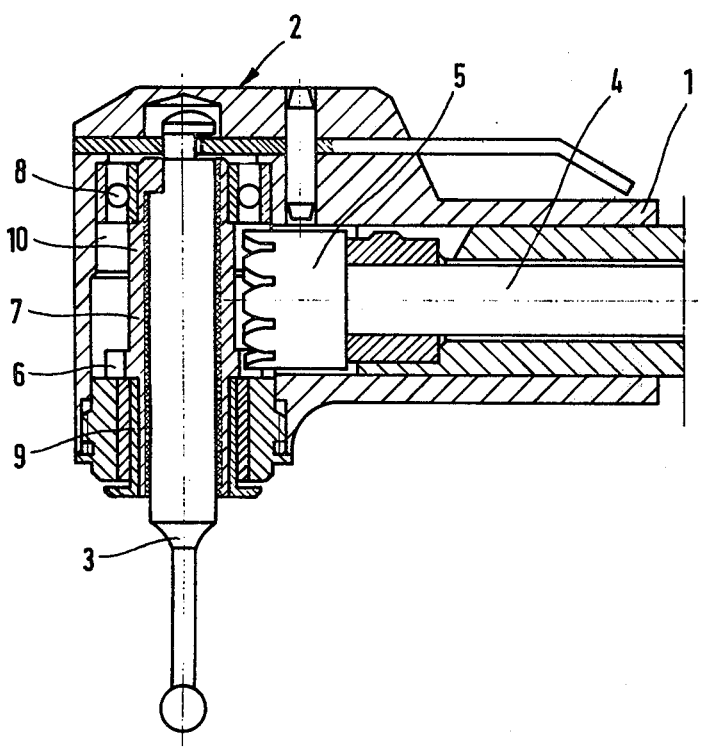
FIG. 1 illustrates a sectional view of the head portion of a dental elbow in which a guide sleeve is utilized for directly supporting the shank of a dental treatment tool.
Figure 2:
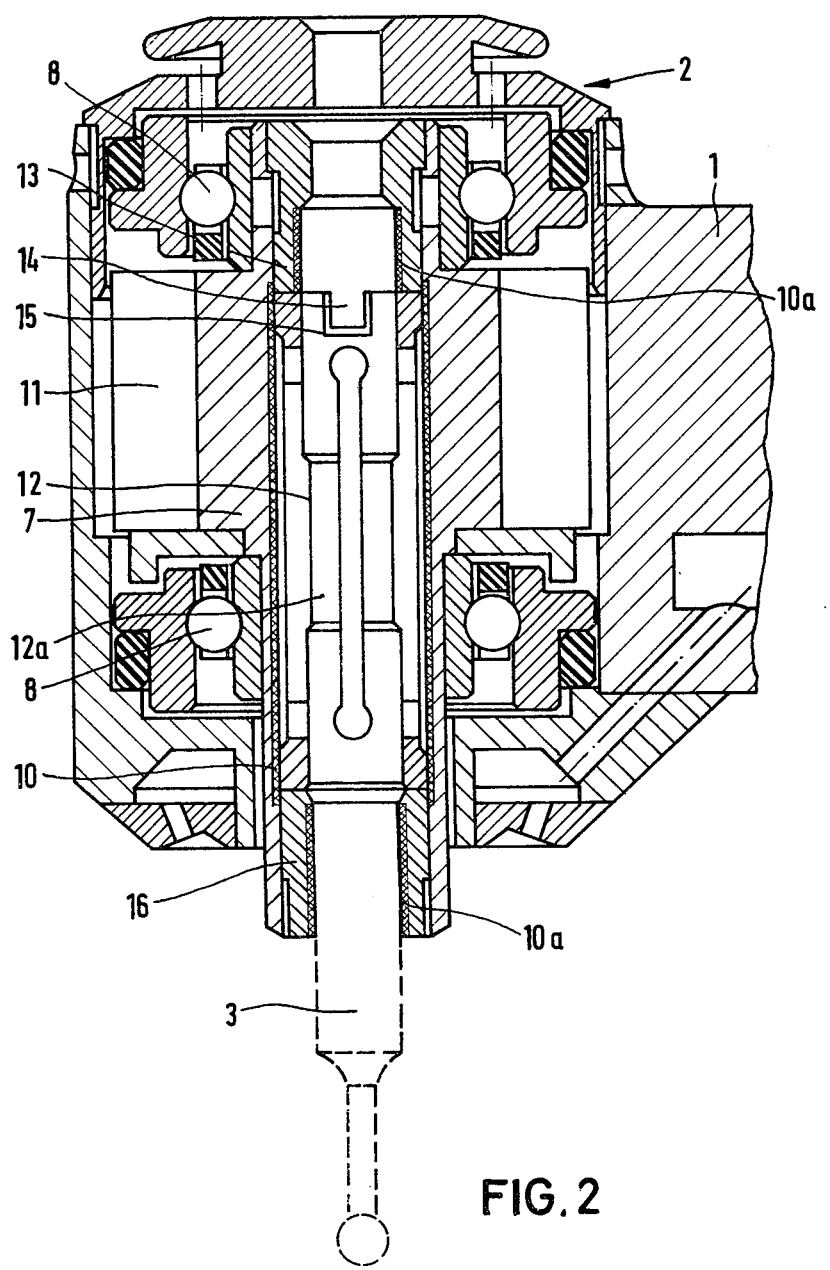
FIG. 2 illustrates a sectional view of the head portion of a dental elbow in which a guide sleeve supports the shank of a dental treatment tool through the intermediary of a collet.

In FIGS. 1 and 2 there is shown the shank 1 of a dental elbow, with the shank extending into the elbow headpiece 2.

In the embodiment of FIG. 1, rotation is imparted to a dental treatment tool 3 through a rotary drive force applied thereto by a drive shaft 4. In order to effect the foregoing, the drive shaft 4 includes a drive spur gear 5 which cooperated with a pinion gear 6 on the guide sleeve 7. The guide sleeve 7 is supported at its upper end within the headpiece 2 by means of a ball bearing 8 and its lower end through a bearing bushing 9. The inner annular wall of the guide sleeve 7 is provided with a coating 10 which has a hardness of at least 1800 HV (Vickers hardness) at a test load of 0.2 kg. The guide sleeve may be constituted of a hardened metal or alloy, preferably of a hardness of 40 to 58 Rockwell C. Furthermore, the coating should have a thickness preferably in the range of 0.001 to 0.03 mm having a surface roughness depth not exceeding 1.5 $\mu z$.

In the embodiment of FIG. 2 there is disclosed a turbine-elbow headpiece 2 in which the guide sleeve 7 is formed as a turbine rotor having a hollow shaft 7'. The turbine blades are designated by reference numeral 11. The driving air which impinges against turbine blades 11 is conveyed through the elbow shank 1. The outlet for the exit air is effected in a well known manner not essential for an understanding of the invention.

The guide sleeve 7 is supported at both ends thereof in the headpiece 2 through the intermediary of ball bearings 8. In the interior of the hollow shaft formed guide sleeve 7 there is located a collet 12 which is adapted to retain the shank of a tooth treatment tool 3. The rigid rotational connection between the guide sleeve 7 and collet 12 is obtained through an insert member 13 which is rigidly pressed or adhesively fastened into the interior of the hollow shaft formed by the guide sleeve, and which includes a follower 14 projecting into a complementary recess 15 in the collet 12. The resilient tension tongues of the collet 12 are designated by reference numberal 12a. At the lower end of the guide sleeve 7, shown in FIG. 2, there is provided in a similar manner an insert member 16 which secures the collet 12 against dropping out of the sleeve.

The inner annular wall of the guide sleeve is herein provided with a coating 10 which has the same physical properties as that in the embodiment of FIG. 1. In the region of the rigid compressive contact between the guide sleeve 7 and the insert members 13 and, respectively 16, there is provided this coating on the inner annular surfaces of the insert members. In this region the coating is designated by reference numeral 10a. In these above-mentioned regions, the inner surfaces of the insert members is to correspond with the inner surface of the guide sleeve beyond these regions.

Figure 3:
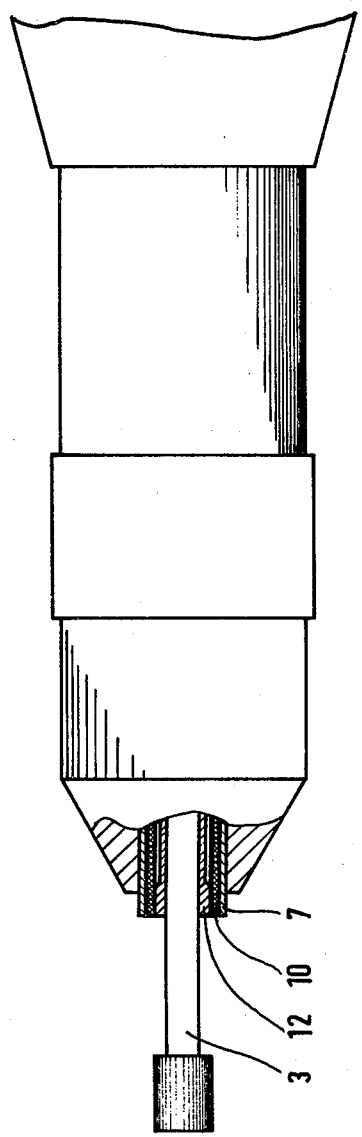
FIG. 3 illustrates a sectional view of the tip of a straight dental handpiece in which a guide sleeve supports the shank of a dental treatment tool through the intermediary of a collet.

The embodiment illustrated in FIG. 3 largely corresponds with that of FIG. 2, however, in FIG. 3 the invention relates to a straight dental handpiece, and wherein, in another manner, the collet 12 is at its upper end (not shown) connected for example, by means of screwing, rotatably-and-slide-fast with the guide sleeve 7. In this case, the coating 10 again extends, as in FIG. 1, directly to the inner surface of the guide sleeve 7.

While there has been shown what is considered to be the preferred embodiment of the invention, it will be obvious that modifications may be made which come within the scope of the disclosure of the specification.

What is claimed is:

1. In a dental handpiece having a headpiece; a guide sleeve formed of hard metal; and means rotatably supporting said guide sleeve within said headpiece, said guide sleeve being adapted to support the shank of a dental treatment tool interiorly thereof, the improvement comprising; a coating formed essentially of chromium and metal carbide being provided on at least the annular inner wall surface of the guide sleeve, said coating having a hardness of at least 1800 Vickers hardness at a test load of 0.2 kg.

2. An improvement as claimed in claim 1, said coating having a thickness of approximately 0.001 to 0.03 mm.

3. An improvement as claimed in claim 1, said coating being smoothed to a roughness depth of 1.5 $\mu z$ maximum.

4. An improvement as claimed in claim 1, said guide sleeve being formed of a hardened metal having a hardness in the range of 40 to 58 Rockwell C.

* * * * *